US00PP29194P2

(12) United States Plant Patent
Hansen

(10) Patent No.: US PP29,194 P2
(45) Date of Patent: Apr. 3, 2018

(54) ×MANGAVE PLANT NAMED 'LAVENDER LADY'

(50) Latin Name: *×Mangave×Agave*
Varietal Denomination: Lavender Lady

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,442

(22) Filed: Jan. 13, 2017

(51) Int. Cl.
*A01H 5/12* (2006.01)

(52) U.S. Cl.
USPC ..... Plt./373

(58) Field of Classification Search
USPC ..... Plt./373, 372
CPC ..... A01H 5/12
See application file for complete search history.

(56) References Cited

U.S. PATENT DOCUMENTS

PP4,201 P * 1/1978 Cobia ..... A01H 5/12
Plt./372

* cited by examiner

*Primary Examiner* — Kent L Bell

(57) ABSTRACT

A new and unique ×*Mangave* plant named 'Lavender Lady' characterized by a compact mound of short, broad, fleshy, nearly flat, smoky purple foliage becoming green with age. New leaves develop heavy, irregular, typically overlapping underlying purple-lavender spots and soft, flexible creamy-colored teeth.

1 Drawing Sheet

Botanical classification: hybrid; ×*Mangave* times *Agave*.
Variety denomination: 'Lavender Lady'.

BACKGROUND OF THE INVENTION

The present invention relates to the new and distinct ×*Mangave* hybrid plant, ×*Mangave* 'Lavender Lady' hybridized by the inventor at a wholesale perennial nursery in Zeeland, Mich., USA as cross between ×*Mangave* 'Bloodspot' (not patented) as the female or seed parent times an unnamed selection of *Agave attenuata* (not patented) as the male or pollen parent. The cross was performed in the Jan. 3, 2012 and seeds were harvested and sown later on Aug. 8, 2012. Through trials at the same nursery the plant was originally assigned the breeder code XMANG-12-36-06. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of ×*Mangave* 'Lavender Lady' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

×*Mangave* 'Lavender Lady' differs from its parents as well as all other *Manfreda, Agave* and ×*Mangave* known to the applicant. Compared with the female parent the foliage of the new plant is shorter and more compact, the foliage is broader and more lavender-purple colored and lacks the larger spots. Compared with the male parent the new plant is more compact with shorter foliage that is more lavender-purple colored, the teeth are not as hard and it has more leaves per plant. The most similar known cultivars are ×*Mangave* 'Moonglow' U.S. Plant patent application Ser. No. 15/330,178 and ×*Mangave* 'Pineapple Express' U.S. Plant patent application Ser. No. 14/999,084. Compared with 'Moonglow' the new plant has shorter and broader leaves that are more outright with smaller spotting that nearly covers the entire top surface. Compared to 'Pineapple Express' the new plant has shorter and broader leaves that project more outwardly and less upward, and the spotting is smaller and covers more of the leaf surface.

The new plant, 'Lavender Lady', is unique from all of the above cultivars and all *Agave,* ×*Mangave* and *Manfreda* known to the inventor by the following combined traits:

1. Compact mound of short, broad, fleshy, nearly flat foliage;
2. Foliage develops heavy, irregular, smoky purple with typically-overlapping underlying purple-lavender spots throughout upper and lower surfaces, becoming green with age;
3. Teeth on leaves are soft and flexible;
4. Moderate to rapid growth rate.

BRIEF DESCRIPTION OF THE DRAWING

The photograph of ×*Mangave* 'Lavender Lady' demonstrates the overall appearance of the new plant including the unique traits as a two-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

The illustration shows the new plant having been grown in a container with foliage color changes, teeth and apical spines.

DETAILED BOTANICAL DESCRIPTION

The following descriptions and color references are based on the 2001 edition of The Royal Horticultural Society Colour Chart except where common dictionary terms are used. The new plant, ×*Mangave* 'Lavender Lady', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Parentage: ×*Mangave* 'Bloodspot' as female (seed) parent and an unnamed selection of *Agave attenuata* as male (pollen) parent.

Propagation: Division of side shoots and sterile shoot-tip tissue culture.

Time to initiate roots from tissue culture: About 21 days.

Growth rate: Moderate to rapid.

Crop time: About 12 to 14 weeks to finish in a 3.8 liter container from a 35 mm tissue culture growing at about 21° C.

Rooting habit: Fleshy, lightly branching, with roots up to 15 cm long.

Root color: Nearest RHS 158C.

Plant shape and habit: Succulent herbaceous perennial with basal rosettes of about 60 leaves radially emerging outwardly from central stem, producing a radially-symmetrical, rounded mound.

Plant size: Foliage height about 28.0 cm tall from soil line to the top of the leaves and about 43.0 cm wide at the widest point slightly below soil line in container.

Foliage description: Ovate to rhombic; simple; margins finely dentate with flexible teeth, thick and fleshy; teeth about 1.0 mm long and spaced about five to six teeth per centimeter; apex acute with terminal spine; slightly attenuate and truncate, sessile; flat; bi-laterally symmetrical; with underlying dark burgundy spots about 1.0 mm to 2.0 mm long and wide frequently touching or overlapping to almost solid spotting.

Leaf size: To about 18.0 cm long, about 5.0 cm wide approximately two-thirds toward apex; and about 10.0 mm thick at base; average about 15.5 cm long, 2.8 cm wide and 8.5 mm thick.

Foliage fragrance: None observed.

Leaf blade color:

*Adaxial* (*young*).—Nearest RHS 138B with spots intensifying with ultraviolet light exposure to between RHS 187A and RHS N187A.

*Abaxial* (*young*).—Nearest RHS 138B with spots intensifying with ultraviolet light exposure to between RHS 187A and RHS N187A.

*Adaxial* (*mature*).—Between RHS N189A and RHS 189A with spots intensifying with ultraviolet light exposure nearest RHS 187A.

*Abaxial* (*mature*).—Nearest RHS 189A.

*Adaxial* (*lowest leaves*).—Between 137A and RHS 138B.

*Abaxial* (*lowest leaves*).—Between RHS 138B and RHS 138C.

*Teeth*.—Nearest RHS 160C.

Petiole: Leaves sessile.

Veins: Parallel; not distinct abaxial or adaxial.

Flower description: Not yet observed.

Fruit and seed not observed.

Disease resistance: ×*Mangave* 'Lavender Lady' has not been observed to be resistant to diseases beyond that which is normal for ×*Mangave, Agave* or *Manfreda*. The new plant is xeromorphic and survives well with minimal water once established. The new plant is hardy at least from USDA zone 10. Full extent of winter hardiness has not been tested.

It is claimed:

1. A new and distinct cultivar of ornamental ×*Mangave* plant named 'Lavender Lady' as herein described and illustrated, suitable for the garden or as a potted plant in the garden or home.

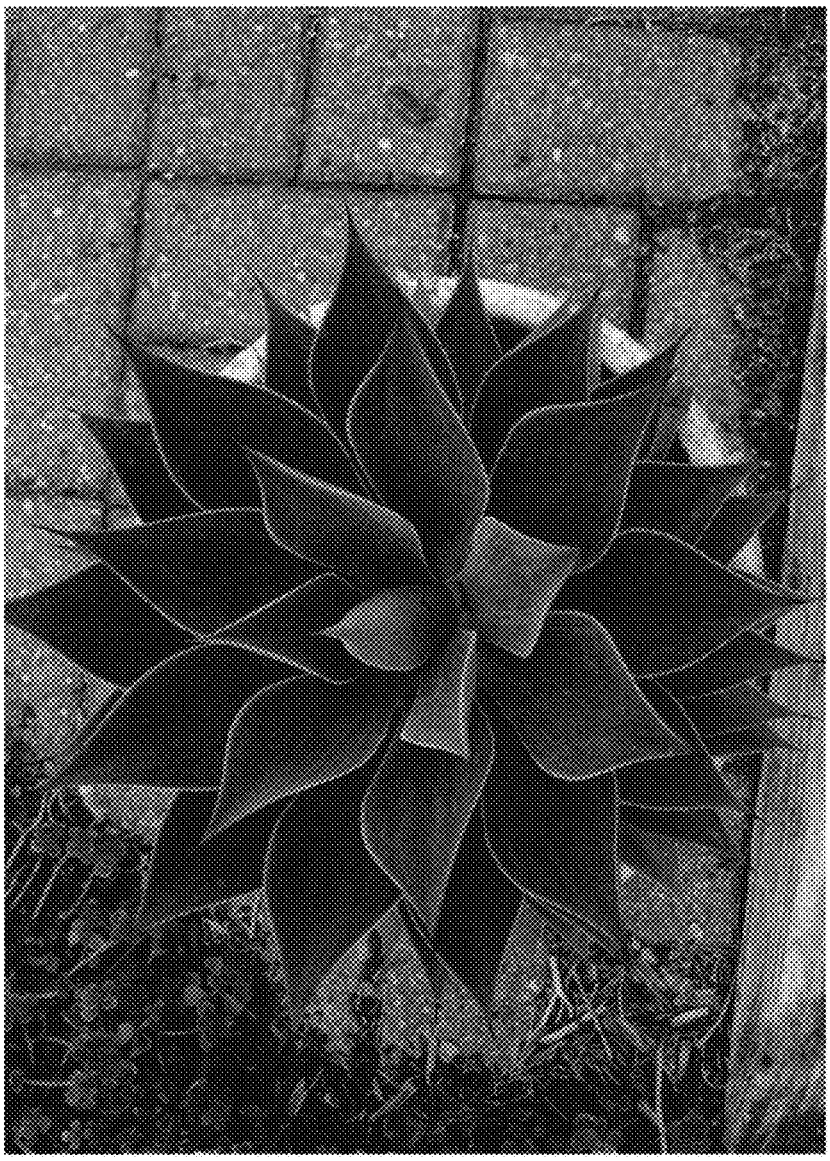

* * * * *